United States Patent [19]

Manns

[11] Patent Number: 5,047,215

[45] Date of Patent: Sep. 10, 1991

[54] MULTIWELL TEST PLATE

[75] Inventor: Roy Manns, Belmont, Mass.

[73] Assignee: Polyfiltronics, Inc., Rockland, Mass.

[21] Appl. No.: 530,913

[22] Filed: May 30, 1990

Related U.S. Application Data

[62] Division of Ser. No. 745,877, Jun. 18, 1985, Pat. No. 4,948,442.

[51] Int. Cl.$^5$ .......................... C12M 1/12; C12M 1/20
[52] U.S. Cl. .................................... 422/101; 210/473; 435/301; 435/311
[58] Field of Search ................ 422/101; 435/301, 311; 210/473, 927

[56] References Cited

U.S. PATENT DOCUMENTS 4,246,339 1/1981 Cole et al. ...................... 422/101 X
4,526,690 7/1985 Kiovsky et al. ................ 422/101 X Primary Examiner—Jill Johnston
Attorney, Agent, or Firm—Gaston & Snow

[57] ABSTRACT

A micro-titre test plate includes a thermoplastic incubation tray having an array of a plurality of wells extending therethrough, a filter, and a thermoplastic harvester tray for supporting the filter sheet. The harvester tray has a plurality of apertures therethrough arranged to be registerable with the bottoms of the wells in the incubation tray. To prevent cross-talk between the wells along the filter, the facing surfaces of the harvester tray and incubation tray are provided with mating ridges and grooves circumscribing the juncture of each well and aperture. In one embodiment, the ridges and grooves are thermally bonded to one another to provide a fluid-impervious barrier trapping respective filter disks in the juncture of each well and aperture. In another embodiment, the harvester tray is formed of a pair of apertured, thermoplastic sheets nested with respective thermally bonded grooves and ridges to trap the filter, the harvester tray being not necessarily bonded to the incubation tray.

8 Claims, 4 Drawing Sheets

MULTIWELL TEST PLATE

This application is a division of copending U.S. patent application Ser. No. 745,877 filed June 18, 1985 and now U.S. Pat. No. 4,948,442.

This invention relates to biological and biochemical assays, and particularly to a multi-well sampling and filtration device useful in such assays.

Multi-well test plates used for isotopic and nonisotopic in-vitro assays are well known in the art and are exemplified, for example, by those described in U.S. Pat. Nos. 3,111,489, 3,540,856, 3,540,857, 3,540,858, 4,304,865, in U.K. Patent 2,000,694 and in European Patent Application 0,098,534. Typically, such test plates have been standardized in the form of the so-called micro-titre plate that provides ninety-six depressions or cylindrical wells of about 0.66 cm in diameter and 1.3 cm deep, arranged in a 12×8 regular rectangular array spaced about 0.9 cm center to center.

Selected wells in such a test-plate are used to incubate respective microcultures, followed by further processing to harvest the incubated material. Each well typically includes a filtration element so that, upon application of a vacuum to one side of the plate, fluid in each well is expressed through the filter leaving solids, such as bacteria and the like, entrapped in the well. In typical use, specimens from up to ninety-six different individuals may be respectively inserted in corresponding wells in a plate in the course of an assay, the specimens typically all being inserted prior to filtration and completion of the assay.

Heretofore, it has been common practice to manufacture such plates as a multi-layer structure including a single sheet of filter material disposed to cover the bottom apertures of all the wells, the filtration sheet being bonded to the periphery of one or more of the well apertures. Unfortunately, such structure may permit fluid expressed through the filter medium from one well, as by capillary action, gravity or application of pressure, to wick through adjoining portions of the filter medium to the filter medium covering an adjacent well aperture. This mingling of fluids in the filter medium from adjacent wells is known as "cross talk" and is considered highly undesirable inasmuch as it can serve as a source of contamination, interfere with an assay, and cause ambiguity and confusion in interpreting assay results.

Alternatively, as disclosed in U.S. Pat. No. 4,304,865, a micro-titre, multi-layer plate includes a substantially rigid culture tray provided with wells having upstanding edges or rims bounding the wider openings to the wells, and incubation is achieved while the culture tray is held "upside-down", i e. the rims are disposed below the sheet. To harvest material from such wells, a sheet of filter paper is placed over the top of a substantially rigid harvester tray having a like plurality of wells, each disposed and dimensioned to provide a tight push-fit with respect to the periphery of the rim of a corresponding well in the culture tray. The latter is then pressed against the harvester tray to push the rims into the wells in the latter, thereby die-cutting filter discs from the filter tray. A vacuum applied to the bottom surface of the harvester tray draws fluid from the culture tray wells through the respective filter discs. The efficacy with which such discs are formed and function depends upon many factors such as the smoothness and sharpness of the rims, the precision of the fit of the rims into the harvester wells, the uniformity and tear-strength of the filter paper, and many others. Further, the press fit of the harvester tray with the filter tray does not guarantee that there will be no cross-talk between adjacent wells.

A principal object of the present invention is to, therefore, provide multi-well, multi-layer test plates incorporating filter elements, in which plates the cross talk problem has been overcome. Another object of the present invention is to provide a method of making multi-well test plates that overcomes the problem of cross talk.

Yet another object of the present invention is to provided such a test plate in which one or more of the individual filter elements associated with each well can readily be detached, either singly or in groups, for introduction into various test solutions or assays.

To these ends, the present invention comprises a multiwell test plate apparatus comprising a substantially rigid planar first or culture tray having a plurality of wells formed therein, and a second substantially rigid planar second or harvester tray having a plurality of apertures formed therein and registerable respectively with the plurality of wells in the first tray. Means are provided for defining a plurality of raised peripheries disposed respectively about each of the plurality of wells (or apertures as the case may be) in one tray, means defining a corresponding peripheral depression being similarly provided if desired but not necessarily, with respect to each of the corresponding apertures (or wells as the case may be) in the other tray. The raised peripheries of the first tray are bonded to a surface of the second tray, as by fusion, to provide a fluid-impervious barrier. Because filter means, in the form of a filter sheet, may be disposed between the first and second trays at the time of bonding, the bonding operation automatically provides filter discs between each well and corresponding aperture, but fluid conduction between the filter discs is positively prevented because the bonded raised peripheries provide a barrier to fluid transport between wells. Lastly, means defining a vacuum plenum or manifold may be positioned adjacent the other surface of the second tray.

In yet another version of the present invention, the second tray as described above is formed of two nesting plates intended and configured to trap the filter sheet between them in a manner preventing cross-talk. This multiple plate version can then be a disposable unit because it is not necessarily bonded to either the culture tray or vacuum manifold. In another embodiment of the multiple plate tray, the latter is scored around the periphery of each filter disc, thereby permitting the tray, after removal, to be snapped apart to detach any desired filter or combination of filters for further processing.

These and other objects of the present invention will in part be obvious and will in part appear hereinafter. The invention accordingly comprises the apparatus possessing the construction and arrangement of parts exemplified in the following detailed disclosure, and the method comprising the several steps and the relation and order of one or more of such steps with respect to the others, the scope of the application of which will be indicated in the claims.

For a fuller understanding of the nature and objects of the present invention, reference should be had to the following detailed description taken in connection with the drawings wherein.

Figure 1:
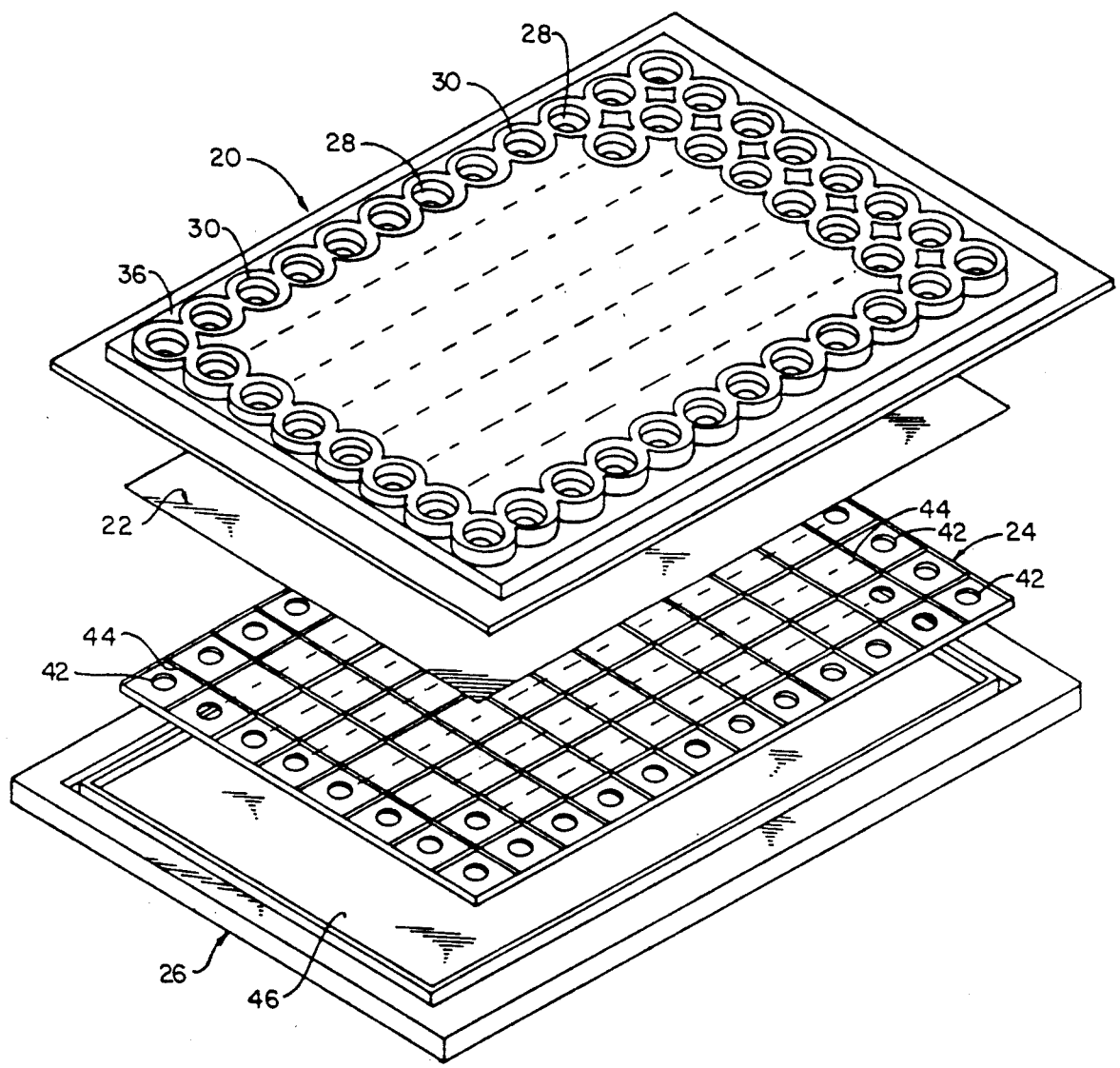
FIG. 1 is an exploded isometric view of a multi-well filter apparatus made according to the principles of the present invention.
Figure 5:
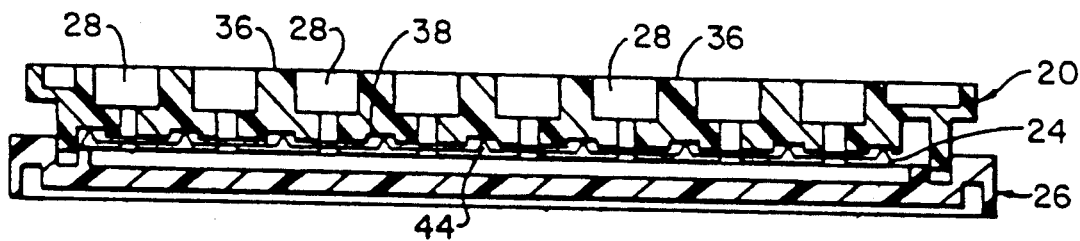
FIG. 5 is an enlarged cross-section of an assembed form of the apparatus of FIG. 1, before fusion.

FIGS. 1 and 5 illustrate the four basic elements of the apparatus of the invention: culture tray 20, filter sheet 22, harvester tray 24 and base enclosure 26.

Culture tray 20 is a rectangular body or slab having two opposed, substantially planar surfaces, tray 20 being formed of a substantially rigid, water-insoluble, fluid-impervious, thermoplastic material chemically non-reactive with the fluids to be employed in the assays to be carried out with the apparatus. The term "substantially rigid" as used herein is intended to mean that the material will resist deformation or warping that would prevent maintainence of a substantially planar surface, under light mechanical or thermal load, although the material may be somewhat elastic. Suitable materials are polyvinyl chloride with or without co-polymers, polyethylenes, polystyrenes, polyvinylidine chloride, and the like. The preferred material is a polysulfone, for it provides very low, non-specific protein binding, making it specially suitable for use with samples, such as blood, viruses and bacteria, incorporating protein of interest.

Figure 2:
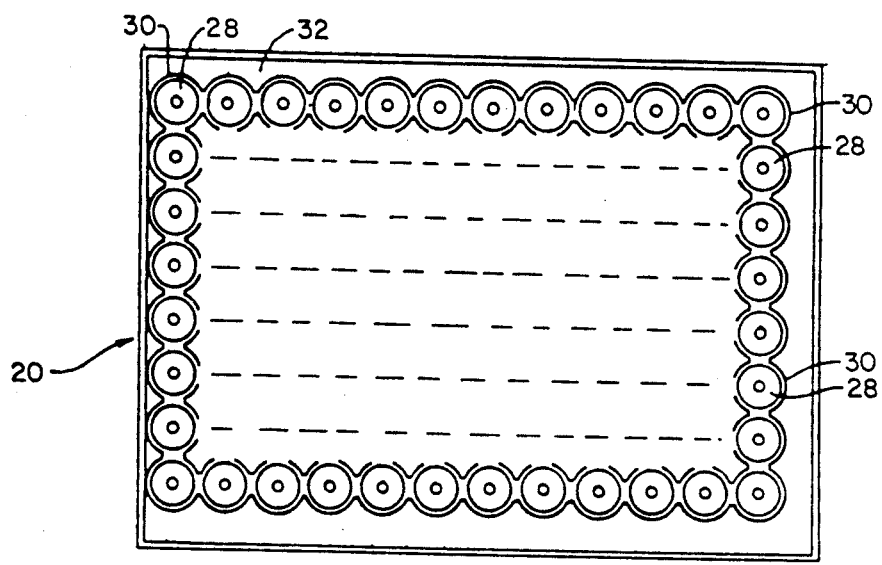
FIG. 2 is a plan view of the upper surface of the culture tray of the embodiment of FIG. 1.
Figure 3:
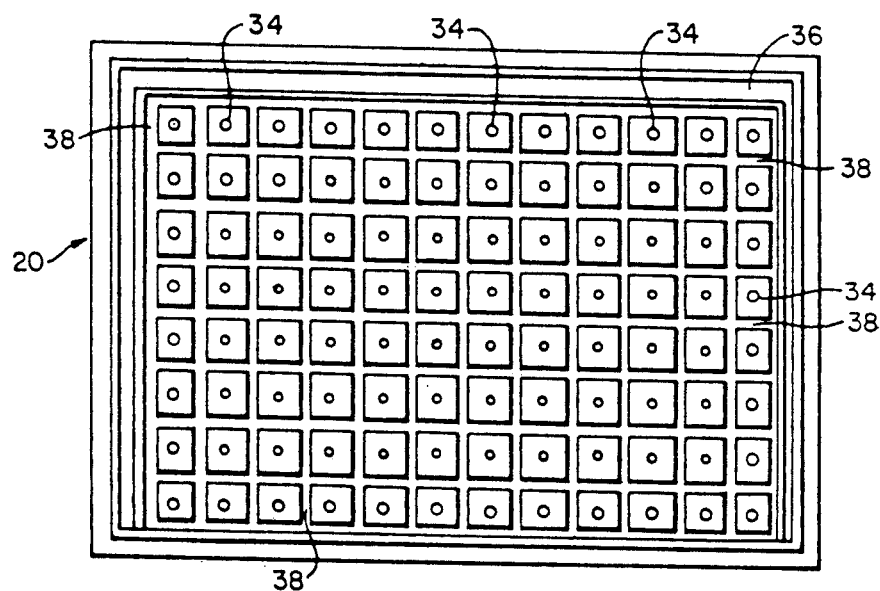
FIG. 3 is a plan view of the lower or underneath surface of the culture tray of FIG. 2.

As shown particularly in FIGS. 2 and 3, tray 20 is formed with a plurality (typically 96) of identical, wells 28 each extending from a respective opening 30 in planar surface 32 of tray 20 to an another opening 34 in opposed surface 36 of tray 20. The depth of each well is determined by the thickness of tray 20, and together with the diameter of the well, determines the volume of liquid that the well can hold. For example, each well is about 0.66 cm. in diameter and 1.3 cm. deep. The plurality of wells is preferably arranged in a 12×8 regular rectangular array spaced about 0.9 cm. center-to-center. The wells may be cylindrical, conical or have other configurations depending upon the wishes of the designer or user. In one embodiment, each opening 34 in the underneath surface 36 of tray 20 is circumscribed with a groove or channel 38. The latter may be a square as shown in FIG. 3 or may take other geometrical shapes such as circles and the like.

Figure 4:
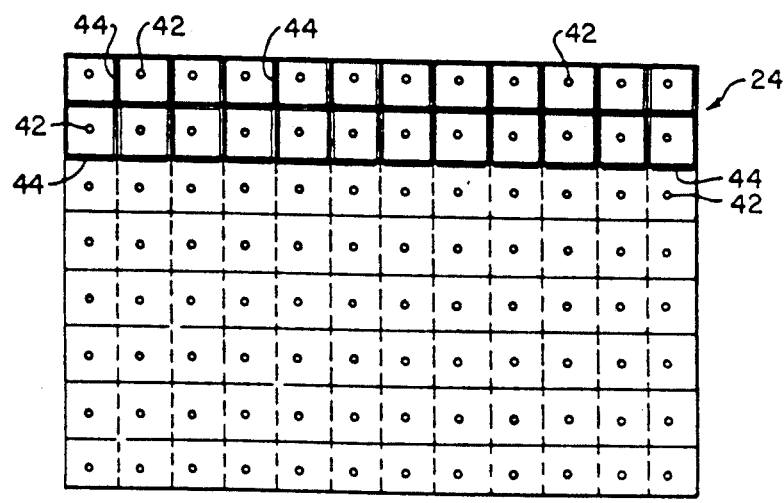
FIG. 4 is a plan view of the upper surface of the harvester tray of the embodiment of FIG. 1.

As shown in FIG. 4, harvester tray 24 is also a rectangular body or slab having at least one substantially planar surface 40, tray 24 being formed of a substantially rigid, water insoluble, fluid-impervious thermoplastic material the same as or similar to that used to form tray 20. Tray 24 is provided with a plurality of apertures 42 extending therethough from surface 40, apertures 42 being the same in number, arrangement and spacing as wells 28 so that apertures 42 can register with openings 34 when surface 40 is adjacent and parallel to surface 36 as shown in FIG. 5. In one embodiment, as shown particularly in FIG. 4, each aperture 42 is circumscribed at surface 40 with upstanding ridge 44. The geometrical shape of the latter should match that of channel 38 and the width of ridge 44 should be small enough to permit the ridge to mate with channel 38 when trays 20 and 24 are suitably positioned and pressed together.

Figure 8:
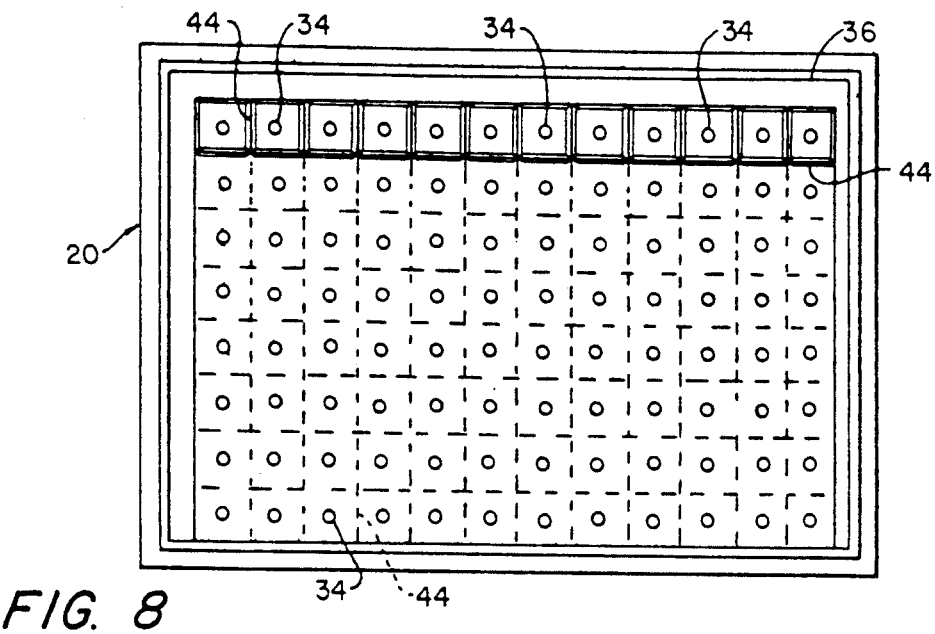
FIG. 8 is a plan view of an alternative form of the lower surface of a culture tray of the present invention.
Figure 9:
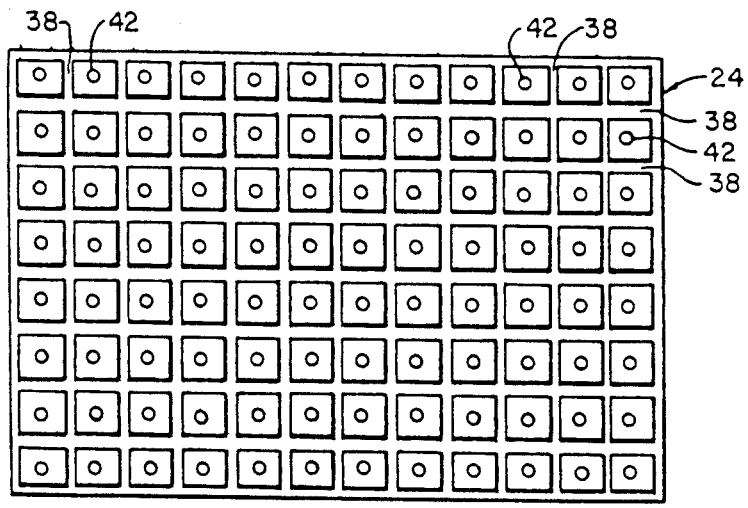
FIG. 9 is a plan view of the upper surface of an alternative form of the present invention for use with the culture tray of FIG. 8.

It should be noted that in an equally acceptable alternative, as illustrated in FIGS. 8 and 9 wherein like numerals denote like parts, ridges 44 are positioned or formed on tray 20 and corresponding channels are then formed on tray 24.

Base enclosure 26 is a rectangular hollow vessel having an opening dimensioned to fit closely around the rectangular periphery of tray 24 so as to provide a closed chamber or penum 46 disposed below tray 24 to provide pneumatic access to openings 34 at the surface of tray 24 opposite to surface 40. The hollow interior of plenum 46 is pneumatically connectable to an external vacuum source through a hosecock extending through a wall of plenum 46. In a preferred embodiment, enclosure 26 is formed of a thermoplastic material the same or similar to that used to form tray 24.

Lastly, disposed between surface 40 of tray 24 and surface 36 of tray 20, at least in the assembly stage of manufacture of the apparatus of the invention, is filter sheet 22. Filter sheet 22 is typically a microporous membrane filter, formed, for example preferably of thermoplastic material such as cellulose acetate, polysulfones, and the like.

Figure 6:
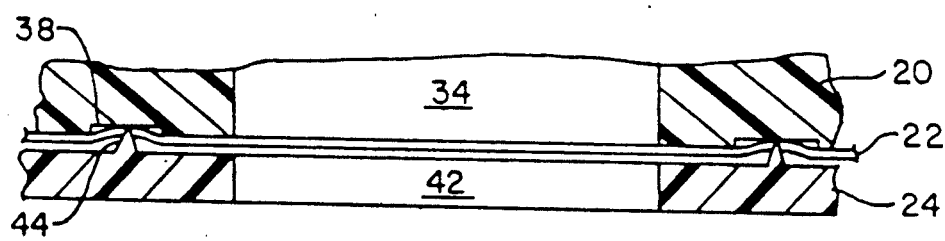
FIG. 6 is an enlarged cross-section of the embodiment of FIG. 5.
Figure 7:
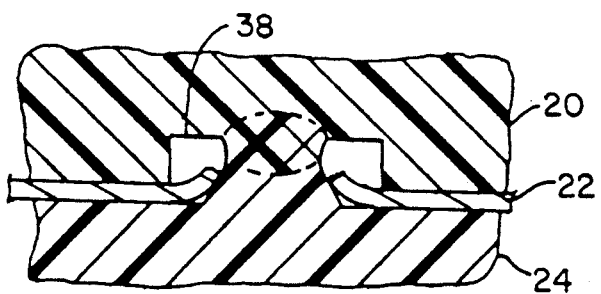
FIG. 7 is the cross-section of FIG. 6 after fusion.

To manufacture the micro-titre plate of the invention, as shown in FIG. 5 and 6, tray 20 is fitted into tray 24 with surfaces 40 and 36 facing one another, filter sheet 22 being engaged therebetween. The trays are disposed so that each opening 34 of each well 28 is registered with a corresponding opening 42 in surface 40. Further, each ridge 44 is therefore mated with a corresponding channel 38. The assemblage is then subjected to pressure, substantially uniformly distributed across the assemblage and directed normally to the planes of surfaces 36 and 40, sufficient to force the top edges of ridges 44 into close contact with the interior surface of channels 38, crushing that portion of filter sheet 22 trapped between the ridges and channels. At the same time, the periphery of enclosure 26 is forced into intimate contact with the periphery of tray 24. The mated edges of the ridges and surfaces of the channels, and the mated peripheries of tray 24 and enclosure 26 are then thermally bonded to one another, preferably by ultrasonic bonding. Alternatively, thermal bonding may also be achieved simply by insert-molding tray 24 directly onto tray 20 with the filter trapped between them. As shown in fragmentary cross-section in FIG. 7, the bonding then creates barrier means in the form of a fluid impervious wall around each juncture of well 38 and opening 34, positively sealing each well from its neighboring wells.

Figure 10:
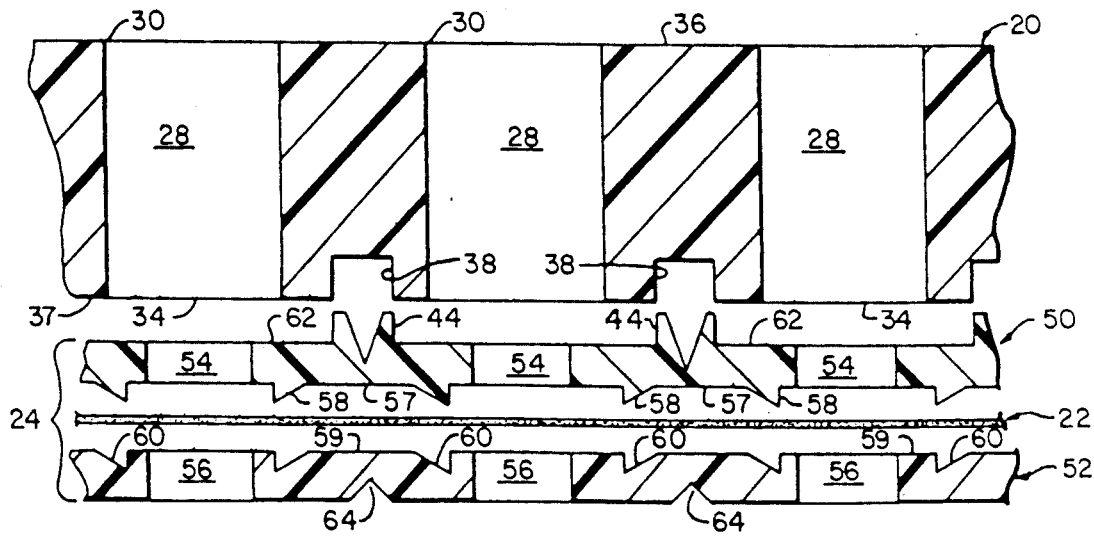
FIG. 10 is a fragmentary, enlarged cross-section of an culture tray, unbonded multiplate harvester tray, and a filter of yet another embodiment of the present invention.

Referring to the embodiment shown in cross-section in FIG. 10, there will be seen typical culture tray 20 and a multiplate harvester tray 24 formed of a pair of mating plates 50 and 52 trapping filter sheet 22 therebetween.

As in the embodiment of FIGS. 1 and 5, culture tray 20 is a rectangular body having two opposed, substantially planar surfaces, and is formed of the similar substantially rigid, water-insoluble, fluid-impervious, thermoplastic material chemically non-reactive with the fluids to be employed in the assays to be carried out with the apparatus. Thus, tray 20 is formed with a plurality of identical wells 28 substantially as shown in FIG. 5, and are shown in FIG. 10 as being cylindrical, although it is understood that conical or other configurations may be provided. In the embodiment shown, each opening 34 in the underneath surface 36 of tray 20 is circumscribed with a channel 38, the channel being in any simple circumscribing geometrical shape desired.

Much as is shown in FIG. 4, harvester tray 24 is also a rectangular body or slab, but in the embodiment of FIG. 10, tray 24 is formed of two nested plates 50 and 52, each of which is preferably made of a substantially rigid, water insoluble, fluid-impervious thermo-plastic material the same as or similar to that used to form tray 20. Plate 50 is provided with a plurality of apertures 54 extending therethough, apertures 54 being the same in number, arrangement and spacing as wells 28 so that apertures 42 can be registered with openings 34. Similarly, plate 52 is provided with a like plurality of apertures 56 in like array. Each aperture 54 is circumscribed on surface 57 of plate 50 with a respective upstanding ridge 58 and each aperture 56 on surface 59 of plate 52 is similarly circumscribed with a respective groove or channel 60, it being understood however that which particular plate bears channels 60 or ridges 58, is a matter of choice. Of course, the geometrical shape of the grooves and channels should match, the width of the ridges being small enough to mate with the corresponding channel when plates 50 and 52 are aligned and pressed together. Each aperture 54 on surface 62 of tray 50 (intended to face toward tray 20) is circumscribed with an upstanding ridge 44 as in the embodiment of FIG. 1. The geometrical shape of the ridges latter should match those of channels 38 and the width of each ridge 44 should be dimensioned to permit the ridge to form a tight fit in the corresponding channel 38 when trays 20 and 24 are suitably positioned and pressed together.

Disposed between the mating surfaces surface plates 50 and 52, at least in the assembly stage of manufacture of the embodiment of FIG. 10, is filter sheet 22, which is substantially identical to the filter sheet employed in the embodiment of FIG. 1.

Importantly, the outside surfaces of multiplate tray 24, are scored to permit the tray to be broken along the score lines into segments each containing an integral multiple of a dual aperture and the trapped filter disc. To this end, in the embodiment shown in FIG. 10, plate 52 is provided on surface with deep scoring or grooves 64 circumscribing each aperture 56. Similar and matching grooving 66 is provided on surface 62 about each aperture 54 in plate 50. In the form shown, each groove 66 is conveniently located in the upper edge of a corresponding ridge 44, but many other configurations and locations can be provided for the matching or registered grooves 64 and 66.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. Filtration apparatus comprising, in combination:
    a substantially flat, thermoplastic culture tray having at least one well therein extending between open ends on opposite flat surfaces of said tray;
    a substantially flat, thermoplastic harvester tray having at least one opening therethrough, said harvester tray being disposed with respect to said culture tray so that each said opening is adjacent and registered with each said well;
    filtration means extending across each said opening; and
    barrier means formed as a fluid-impervious wall circumscribing and joining together the peripheries of each registered well and opening, said wall being formed of the thermoplastic material of said trays.

2. Filtration apparatus as defined in claim 1 wherein each said wall is thermally bonded to said trays.

3. Filtration apparatus as defined in claim 1 wherein said trays are formed of a polysulfone polymer.

4. Filtration apparatus as defined in claim 1 including a plurality of said wells and a like plurality of said openings, said wells being arranged in a regular array;
    that surface of said harvester tray facing said culture tray having one of a mating channel and ridge circumscribing each of said openings;
    that surface of said culture tray facing said harvester tray having the other of said mating channel and ridge circumscribing each of said wells;
    the juncture of each of said ridge and channel being thermally bonded to one another to form said wall.

5. Filtration apparatus as claimed in claim 4 including a vacuum manifold disposed adjacent the opposite surface of said harvester tray.

6. Filtration apparatus as claimed in claim 4 wherein said manifold is thermally bonded to the periphery of said harvester tray.

7. Filtration apparatus as claimed in claim 1 wherein said harvester tray includes a pair of substantially flat plates, each having an array of openings extending therethrough and registerable with one another and with corresponding wells in said culture tray;
    a first surface of the first of said plates being adapted to face said culture tray and having one of a first mating channel and first ridge circumscribing each of the openings in said first tray;
    the surface of the harvester tray facing said first surface of said first tray having the other of said first mating channel and ridge circumscribing each of said wells;
    each said first ridge and channel being fittable snugly together to form said barrier means;
    the opposite surface of said first plate having one of a second mating channel and second ridge circumscribing each of said openings in said second plate;
    a facing surface of said second plate having the other of said second mating channel and ridge circumscribing each of said openings in said second plate;
    filter means disposed across each of said openings in said plates; and
    the juncture of each of said second ridge and channel being thermally bonded to one another to form a fluid-impervious wall.

8. Filtration apparatus as claimed in claim 7 wherein means scoring said plates so that said trays may be broken apart along said scoring into segments each containing an integral multiple of a registered pair of openings and said filter means.

* * * * *